Figures 1, 2:
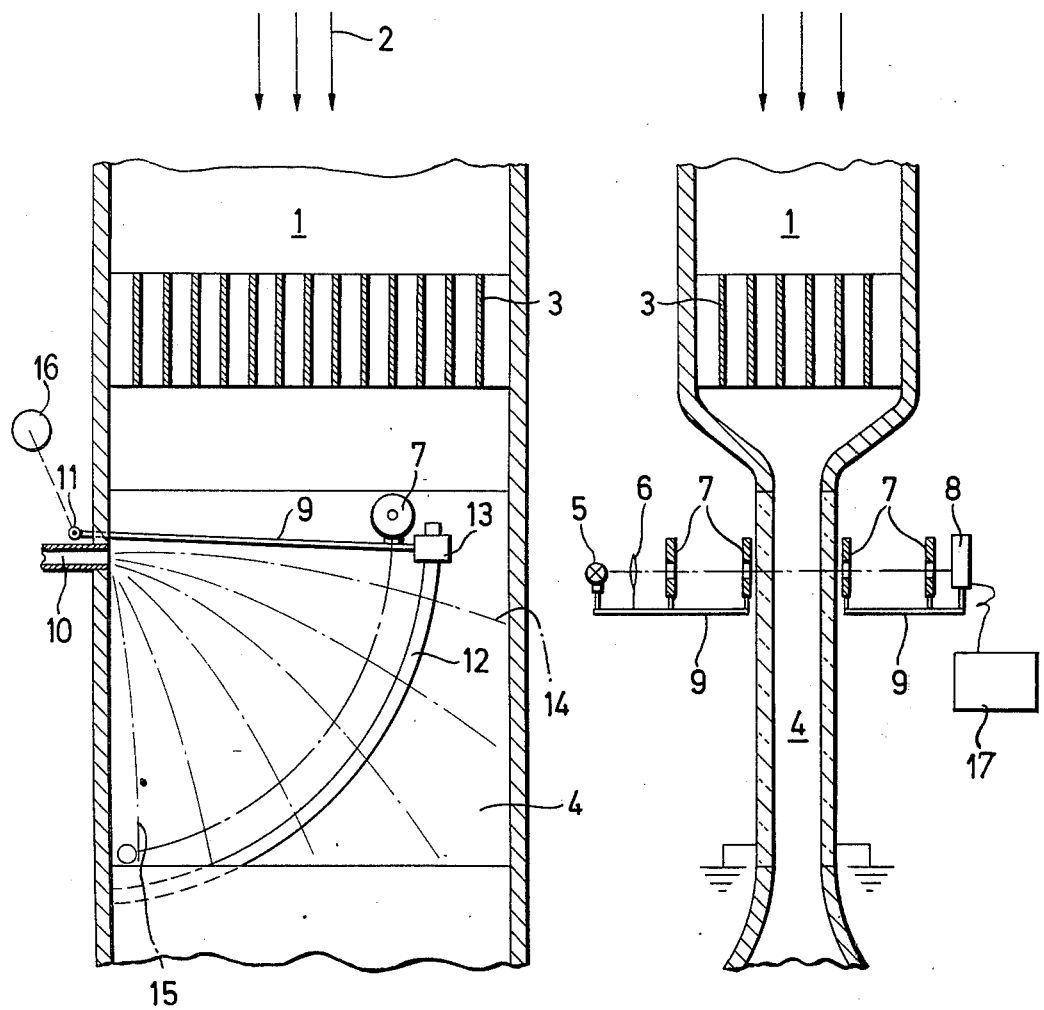

United States Patent [19]
Leschonski et al.

[11] 3,952,207
[45] Apr. 20, 1976

[54] METHOD AND MEANS FOR DETERMINATION OF PARTICLE SIZE DISTRIBUTIONS IN A MASS FLOW OF A GRANULAR MATERIAL

[76] Inventors: Kurt Leschonski, Am Silbersegen 8, 3392 Clausthal-Zellerfeld; Hans Rumpf, Hans-Jakob Strasse 12, 75 Karlsruhe, both of Germany

[22] Filed: June 30, 1975

[21] Appl. No.: 591,844

Related U.S. Application Data

[63] Continuation of Ser. No. 437,034, Jan. 28, 1974, abandoned.

[30] Foreign Application Priority Data

Feb. 1, 1973   Germany............................ 2304879

[52] U.S. Cl. ............................ 250/573; 73/432 PS; 250/576; 356/102
[51] Int. Cl.² ........................................ G01N 21/26
[58] Field of Search ........... 250/573, 574, 575, 576, 250/222 PC; 356/102, 103, 104, 208; 73/28, 432 PS; 209/134, 135, 136, 137, 143, 144, 210, 211; 235/92 PC; 324/71 PC

[56] References Cited
UNITED STATES PATENTS

| | | | |
|---|---|---|---|
| 3,225,296 | 12/1965 | Roth .................................... | 250/573 |
| 3,315,066 | 4/1967 | Muta et al. ...................... | 73/432 PS |
| 3,377,597 | 4/1968 | Muta................................. | 356/102 |
| 3,449,567 | 6/1969 | Oliver et al...................... | 73/432 PS |
| 3,739,180 | 6/1973 | Carlson........................... | 356/102 |

FOREIGN PATENTS OR APPLICATIONS

| | | |
|---|---|---|
| 1,013,446 | 8/1957 | Germany.......................... 73/432 PS |
| 2,019,687 | 7/1970 | France |

OTHER PUBLICATIONS

"A New X-Ray Sedimentometer", Allen et al., Journal of Physics E: Scientific Instruments, 1970, V. 30

*Primary Examiner*—Alfred E. Smith
*Assistant Examiner*—D. C. Nelms
*Attorney, Agent, or Firm*—Hill, Gross, Simpson, Van Santen, Steadman, Chiara & Simpson

[57] ABSTRACT

Method and means for determining the particle size distribution in a flow of granular material in the particle size range of 1 $\mu$m to several millimeters by introducing into a constant velocity stream of a carrier medium, preferably transversely thereof, a stream of the material to be analyzed, said introduction being effected at a constant velocity within a measuring time period, and the velocities of said two streams being so coordinated as to cause the individual particle size classes to be carried along separate particle paths in a fan-shaped pattern while being subjected to an electromagnetic radiation, and determining the particle quantities corresponding to the individual particle size classes in the fan-shaped stream of material from the extinction or absorption of said electromagnetic radiation.

9 Claims, 2 Drawing Figures

METHOD AND MEANS FOR DETERMINATION OF PARTICLE SIZE DISTRIBUTIONS IN A MASS FLOW OF A GRANULAR MATERIAL

This is a continuation of application Ser. No. 437,034, filed Jan. 28, 1974, now abandoned.

This invention relates to a method for determination of the particle size distribution in a mass flow of a granular material in the particle size range from approximately 1 $\mu$m to several millimeters, as well as to a device for carrying out said method.

For the control or regulation, supervision and product control of processes for the manufacture of granular products in the abovementioned particle size range it is in many cases necessary to determine the particle size distribution or a characteristic fineness-indicating average value of the induced mass flow, from which value conclusions regarding the progress of the production process can be drawn. If a certain predetermined particle size distribution is decisive for the quality of the obtained product, it is possible to effect optimal setting of individual units, such as grinding machines, separators or segregation apparatus through suitable adjustment measures. In many cases it is due to the short dwelling time of the product in said units necessary to perform the measuring of the particle size distribution or the characteristic average value as much in parallel as possible with the ongoing production process and as continuously as possible in order to enable the fastest possible corrective intervention in the control cycle and thereby in the product quality.

The measuring of the particle size distribution is ordinarily not performed on the total produced mass flow but only on a partial flow sample which is as representative as possible. Said sample should in view of the statistically greater evidence safety and due to the work and equipment requiring sample-taking and separation consist of a not too small flow mass portion.

The problem of determining a particle size distribution of a representative product flow in parallel with the ongoing production process can according to the invention be solved by introducing the stream of material to be analyzed into a carrier medium stream, preferably transversely of the latter, and with a velocity which within a time period designated as measuring time is constant, said carrier medium stream likewise having constant velocity, and the velocities of the material and the carrier medium stream being so selected that the individual particle classes are moved along different particle paths in a fan-shaped pattern, and that the particle quantities in said individual particle classes are determined from the degree of extinction or adsorption of a radiation, preferably an electromagnetic radiation through the fan-shaped stream.

Advantageously, the invention makes use of the fact that with suitable material charge and with constant feed velocity for material and carrier medium the paths of the individual particle classes in the fan-shaped stream are practically constant in respect of locality, so that the mass proportions of individual particle classes can be established in dependence upon said locality. Thus, with the aid of this method even sample quantities of some 10 kg/h may be advantageously and continuously sub-divided in the carrier medium stream. An essential advantage of the inventive method consists additionally in the fact that the measuring can be carried out without contact and, therefore, no disturbances of the carrier medium stream occur and no adulterations of the mass distribution through mechanical separating means as, for example, in the case of inclusion of one or more cutting edges.

In an advantageous embodiment of the invention it is arranged to have the particle amounts allocated to the individual particle classes determined photo-electrically by means of visible light.

In another advantageous embodiment of the invention it is provided that the particle quantities allocated to the individual particles classes are determined from the adsorption of a radiation of shorter wave length than visible light, preferably a gamma radiation. This has the advantage that even with a relatively great layer thickness in the fan-shaped stream the determination of the particle size distribution can be carried out.

In an advantageous development of the invention it is further provided that the radiation is directed perpendicularly to the plane of the fan-shaped stream in the carrier medium flow, the extinction or adsorption being surveyed over a plane that extends approximately in parallel with the fan-shaped stream and approximately perpendicularly to the course of the particle paths in said stream. A measuring zone extending in this manner gives theoretically the best results. It has, however, only in exceptional cases a geometrically simple shape.

In a further advantageous embodiment it is therefore provided that the measuring zone forms part of a circle, the center of which lies on the side of the material introduction into the carrier medium stream. In the case of comparatively small fan-shaped streams of material a rectilinear measuring zone is advantageous in view of the structural form of a suitable measuring device.

In a development of the inventive method it is further provided that the measuring zone in the fan-shaped stream of material is swept or scanned by means of a punctiform, continuously reciprocated radiation source, and that the extinction or absorption of the radiation is measured at the other side of said stream by means of moving or stationary detectors. Thereby only a minor portion of the fan-shaped stream, limited by the cross-section of the radiation beam, is always surveyed with regard to its extinction or absorption. It is true that a certain distortion of the analysis result is taken into the bargain, as the momentary grain size composition of the supplied material is not measured at one and the same time since through the movement of the radiation source a certain time delay results. This disadvantage is, however, with sufficient frequency of the back and forth movement of the radiation source largely compensated. On the other hand, through the limitation of the zone of the material stream momentarily investigated, which is achieved through the cross-section of the light beam, disturbing stray effects of adjacent granule classes are eliminated and thereby the measuring result is substantially improved.

For certain utilization cases, such as in the use of the analyzing equipment in a heavily dust-laden surrounding in which the use of a moving measuring device would encounter difficulties in practical operation, it is of advantage to dispense with moving parts and to instead thereof penetrate the measuring zone by means of a stationary linear radiation source and measure the extinction or absorption of the radiation at the other side of the fan-shaped stream by means of at least one detector which follows the progress of the radiation source. Again, if a plurality of punctiform detectors arranged side by side are used, so can through suitable coupling either directly the distribution density curve be obtained or, since with regard to the measuring zone in the fan-shaped stream in scanning direction the absolute particle size either increases or decreases from one side, the total penetration curve or the total residue curve for the material flow can be obtained through proper interconnection of adjacent detectors. If a linear detector is used, the measuring slot must be continuously opened or closed, when the sum total curve or the total residue curve is to be measured.

If in the case of moving systems it is desirable to shorten the scanning distance, an advantageous development of the invention makes provisions for moving back and forth across the measuring zone a plurality of equi-distantly arranged punctiform radiation sources through said distance in parallel with the plane of the fan-shaped stream of material.

If a punctiform radiation source of small radiation cross-section (a diameter of a few millimeters) is utilized, then it is feasible with this arrangement to measure the mass proportions of individual particle classes in dependence upon the locality. The punctiform radiation source forms, for example by means of an optical system, diaphragms and a detector corresponding to the radiation type used, for example a photo-element, a measuring device which can be used for measuring the distribution density curve of the material stream fanned out in the carrier medium light beam when moved at least once across the portion of the fan-shaped stream determined by the measuring zone. If this measuring device is now continuously moved back and forth on the path curve, with the total distribution measured once in each direction of movement, then it is possible within a short time to perform very many repeat measurings which can be statistically evaluated, and which substantially enhance the evidential accuracy. The scanning of the measuring zone of the fan-shaped stream can as a rule be carried out in a second, and less.

The radiation, weakened by the solid material particles, is not directly a measure of the particle concentration sought. In the case of the photometric evaluation the Lambert-Beer law forms the basis and the evaluation is effected similarly to the known evaluation with photo-sedimentometers using the cover-stratification method. This evaluation can, for example, be carried out in parallel with the measuring by means of an electronic computer. The distribution density curve obtained in a single or multiple measuring of the fan-shaped stream of material is generally not yet gaged. This is done by placing partial surfaces below the calculated curve in proportion to the total surface below said curve, the latter being a measure of the concentration of the influent stream. The surface portions in predetermined particle classes then represent their mass portions. In order to effect this normalizing the entire fan-shaped material stream must therefore always be gaged. The measuring of an individual particle class with a punctiform stationary measuring system can be used for an absolute measuring only if the concentration or the mass flow of the influent material stream is measured by means of a different method.

In developing the invention it is further of advantage that the measuring zone scanned by the radiation extends sufficiently far for a portion thereof to overlap a region of the particle medium stream that is free from solid material particles. This has the advantage that either the radiation source and/or the conjoint detector after each scanning of the measuring zone of the fan-shaped stream of material is checked against a reference value of the radiation weakening and, if necessary, can be re-adjusted as it occurs without the presence of solid material particles in the carrier medium stream.

If the mass flow of the material supplied to the carrier medium stream is maintained constant, it is in some cases of use sufficient, in advantageous utilization of the invention, to compare the progress of the extinction or absorption measured across the measuring zone, with a predetermined process, a deviation therefrom being used as a signal for an adjustment intervention in the device producing or pre-treating the material to be analyzed.

The invention further relates to a device for carrying out the inventive method, said device being characterized by a flow channel, preferably of rectangular cross-section, in which two oppositely disposed walls, preferably the wider sides, are at least partly permeable by the radiation kind employed, and in which in another wall, preferably one of the narrower sides, a material supply opening is provided, at least one radiation source being provided outside of the flow channel in front of one of said permeable side walls, and at least one detector coordinated with said radiation source being disposed in front of the opposite side wall of the flow channel.

Normally the flow channel extends in the vertical direction. If the velocities of the influent material flow and the carrier medium stream are in excess of about 10 meters per second, the influence of the gravity force on the particle paths may be neglected in the case of particle sizes below about 100 $\mu$m. The flow channel may then extend horizontally or at any other angle of inclination.

In an advantageous embodiment of the inventive device it is provided that at least one source of radiation and at least one detector are connected with a driving device which moves the same in synchronism back and forth over a measuring zone which extends at least across the width of the fan-shaped material stream.

The invention will be further explained below with reference to the accompanying diagrammatical drawing, in which FIG. 1 shows a vertical cross-section through the flow channel, in parallel with the wide side thereof, and FIG. 2 shows a vertical cross-section perpendicular to that of FIG. 1.

The abovementioned particle size range of from 1 $\mu$m to several millimeters can ordinarily not be completely handled in one and the same equipment, at least not with one and the same adjustment setting. Thus, for example the particle size range of from 1 $\mu$m to about 200 $\mu$m is analyzed in a gaseous carrier medium stream and the range between about 100 $\mu$m to several millimeters in a liquid carrier medium stream, e.g. water.

The shown exemplary device for carrying out the inventive method serves for determination of the particle size distribution in the case of solid ingredients having granular sizes up to 0.2 millimeters and is operated with air as a carrier medium. For radiation, light is employed. The device comprises a vertically extending flow channel 1 through which the carrier medium flows downwardly at a predetermined constant velocity (arrows 2). In the channel there is provided a flow equalizer 3 which comprises a plurality of small tubes with very thin walls, arranged in parallel beside each other.

Beyond the flow equalizer the channel narrows transversely of its wider side walls to form a nozzle-like, flat rectangular measuring channel 4. Said wider side walls of the measuring channel 4 are made of a transparent material, such as electrically conductive glass, so that they for discharge of possibly generated static electricity may be grounded.

As shown in FIG. 2, at the outside of one of the wider channel walls a preferably punctiform light source 5 is disposed, the radiation from which is passed through a diagrammatically indicated optical system 6 and suitable diaphragms 7 as a parallel light beam transversely through the measuring channel 4. At the side of the channel opposite to the light source a photocell 8 is coordinated therewith. The light source and the photometer are rigidly interconnected by means of a support beam 9 which is pivotally attached at 11 in the region of the material influent place 10, so that the measuring device is guided along a circular path having its center in the material influent region. By the path of movement of the light source the measuring zone in relation to the fan-shaped stream of material is also determined. At least one free end of the beam 9 is at one side guided on a guide track 12 which together with the guide member 13 forms a reversible linear-motor of known construction. The inventive use of a linear-motor offers above all in structural respect advantages, since even at low movement velocities it is possible to operate without interposition of mechanical gearing.

Instead of as a linear-motor the guide track may also be in the form of a gear rack, so that the movement of the measuring device may be effected over a geared engine rather than the guide member 13. Hydraulic or pneumatic drive means may also be employed.

In operation, a predetermined amount of material is introduced over a feeding means (not shown) through the supply opening 10 at constant speed and roughly perpendicularly to the flow direction of the carrier medium into the measuring channel 4 through which said carrier medium flows downwardly at constant speed. Said amount of material may, depending upon the size of the mass stream to be controlled, consist of a continuously separated sample or the total mass stream itself. Due to the different mass forces of the particles in the individual granule classes and under the influence of the different value of the dragging forces exerted by the carrier medium flow on the particles, the stream of material is fanned out in the gas stream. Due to their greater kinetic energy the path of the largest particles is less curved (compare curve 14) than that of the very smallest particles which practically immediately at the influent opening are seized by the gas stream and entrained along the channel wall (compare curve 15). All other particles move in correspondence to their size along intermediately extending curves and thus constitute the fan-shaped material stream. Due to the predetermined velocity data of gas and material the path curves of the particles in each individual granule class are under certain simplifying assumptions determinable in advance, or they may be established by means of suitable test or calibration materials which are as monodisperse as possible.

If now a light beam is passed transversely through the channel, the extinction of which is measured at the other side of the channel by a photo-cell in one of the photo-multipliers, then the mass proportions of the individual granule classes can after a calibration be determined on the basis of the different extinction of the light beam in the region of the respective particle paths of the granule class in question.

The procedure is similar in the case of other radiation types. For example, in the use of gamma rays as detector a semi-conductor counter or a Geiger counter is inserted for the measuring of the absorption.

In order to render possible a measuring of the mass proportions of the individual granule classes extending over the entire granule spectrum, only one light source coupled with a photo-cell is in the examplary embodiment moved back and forth along the fan-shaped material stream. In this case the different extinction in the individual zones of the fan-shaped material stream is continuously sampled and determined by means of a suitable indicating or registration device which is connected with the photo-cell.

The evaluation is, as previously described, effected similarily to the known evaluation by means of photo-sedimentometers employing the stratification method. The evaluation is generally effected in parallel with the measuring as, for example, by means of an electronic computer. An essential advantage of this arrangement is that for the determination of a single particle size distribution curve it is feasible to scan the fan-shaped material stream repeatedly within a predetermined time period as, for example, a hundred times. The distribution curve thus becomes based upon a great number of measurings which can be statistically evaluated so that, e.g., the accuracy range of the measured distribution curve can be indicated.

The scanning speed of the fan-shaped stream is adjusted to approximately 0.1 meter per second or less, so that the measuring zone in dependence upon the width of the fan-shaped stream can be scanned within a very short time period. Through the use of a linear-motor the measuring device can be passed across the measuring zone in a simple manner at uniform velocity. Instead of a curved path for the linear-motor it is without appreciable distortion of the measuring result also feasible to use a path inclined downwardly from the horizontal by 30°, the deepest point of which is located below the material influent opening 10.

The pivot point 11 for the light source and photometer is located substantially at the apex of the fan so that the arc inscribed will sweep across the fan. The reversible linear motor is illustrated schematically at 16. The output from the photocell is fed into a receiver 17 which measures the energy received. The receiver 17 may also embody electrical circuitry for having an input which is a function of the position of the photocell 8 as it moves along its arcuate path. The mechanism 17 will be calibrated, as hereinabove indicated, on the basis of the predetermined velocity data of gas and material for the path curves of particles for each individual granule class, so that the output of the mechanism 17 will provide usable information. Or, if desired, the mechanism 17 can be constructed so that the output is a direct electrical signal for controlling a mechanism which utilizes the stream of particulate material. Construction of the electrical comparative mechanism of the device 17 will be fully appreciated by those skilled in the art and need not be described in detail.

The invention is not limited to the specific forms thereof shown and described. Rather, the invention is intended to include any and all modifications thereof which come within the spirit and scope of the appended claims.

Where the unit 17 is a computer, it can be programmed by measuring the energy absorbed when passing through particles of a uniform and known size in different trial runs. Then, during actual operation, the computer 17 will have an output which is a function of the comparison of the known trial runs and the operative run providing an accurate indication of the particle range being passed. Also, if desired, the computer 17 can be programmed in accordance with calculations which take into consideration the rate of particle flow, the particle size, the fluid used, the velocity of the fluid, and the path of travel of the energy beam source and the detector. The computer may then furnish a total reading of total energy absorbed for the sweep of the energy transmitting means and receiver in its motion down and back up, or the computer may integrate the energy absorption for different locations in the path of travel.

We claim:

1. A method for the determination of the particle size distribution in a mass flow of a granular material having individual particle classes in the particle size range of 1 μm to several millimeters, comprising the steps of:
    establishing a constant velocity flow of a gaseous carrier medium through a continuous flow channel;
    passing the gaseous carrier medium through a flat walled channel of narrow depth open at its downstream end and being of uniform size along its length and of uniform size across its width so that the velocity of said stream of medium is maintained at a constant value for a time period designated as measuring time which extends for the width and length of said narrow channel;
    introducing a stream of granular material into said carrier medium flow at the upstream end and at one side of said narrow channel transversely of the carrier medium flow;
    selecting the velocity of said material stream and said carrier medium flow in such a manner that individual particle classes of the granular material are carried along separate particle paths in a fan-shaped pattern across the narrow channel;
    establishing a signal transmitting radiation at one wall of the narrow channel through the flow across the depth of the narrow channel;
    and receiving the radiation at the other wall of the channel determining the particle quantities corresponding to the individual particle classes in the fan-shaped stream of the material from the extinction of said radiation.

2. A method for the determination of the particle size distribution in a mass flow of a granular material having individual particle classes in the particle size range of 1 μm to several millimeters in accordance with the steps of claim 1:
    in which the particle quantities corresponding to the individual particle classes are determined by the signal transmitting radiation being of a shorter wavelength than visible light.

3. A method for the determination of the particle size distribution in a mass flow of a granular material having individual particle classes in the particle size range of 1 μm to several millimeters in accordance with the steps of claim 1:
    in which the signal transmitting radiation is in the form of visible light and is measured photoelectrically.

4. A method for the determination of the particle size distribution in a mass flow of a granular material having individual particle classes in the particle size range of 1 μm to several millimeters in accordance with the steps of claim 1:
    in which the signal transmitting radiation is delivered in an arcuate path at one side of the narrow channel and is received by a continually moving receiver at the other side of the channel.

5. A mechanism for measuring the particle size distribution of particulate material containing individual particle classes, comprising in combination:
    means defining a continuous flow channel for a flow stream of particulate material;
    a portion of said flow channel having opposed flat walls to form a thin flat measuring channel portion of relatively wide width open at the downstream end;
    means for directing a gaseous carrier stream through said channel;
    a particle inlet at one side at the upstream end of said measuring channel portion directing particulate material across the measuring channel portion resulting in a particle size distribution in a fan-shaped pattern due to interaction with said gaseous stream;
    a radiation signal transmitter at one side of said channel portion for transmitting a signal across said path;
    and a detector means at the other side of said channel portion measuring the energy received from said signal transmitter to determine the energy absorbed by said material in said path and to determine the distribution of particulate material across the path.

6. A mechanism for measuring the particle distribution of particulate material containing individual particle classes constructed in accordance with claim 5:
    including driving means moving said transmitter and said detector means in a path parallel to the walls of said channel portion.

7. A mechanism for measuring the particle distribution of particulate material containing individual particle classes constructed in accordance with claim 6:
    wherein said path is in an arc having a center substantially at the location where the particulate material enters the channel portion.

8. A mechanism for measuring the particle distribution of particulate material containing individual particle classes constructed in accordance with claim 5:
    wherein said transmitter includes a plurality of transmitting means and said detector means includes a plurality of detectors at spaced locations in an arcuate path along the walls of said channel portion.

9. A mechanism for measuring the particle distribution of particulate material containing individual particle classes constructed in accordance with claim 5:
    wherein said detector means has a driving mechanism for moving it in an arcuate path along the wall of said channel portion for continuously receiving a signal from said transmitter along said path.

* * * * *